US010413559B2

(12) United States Patent
Murofushi et al.

(10) Patent No.: US 10,413,559 B2
(45) Date of Patent: Sep. 17, 2019

(54) METHOD FOR TREATING DEMYELINATING DISEASE

(71) Applicants: OCHANOMIZU UNIVERSITY, Tokyo (JP); SAITAMA MEDICAL UNIVERSITY, Saitama (JP)

(72) Inventors: Kimiko Murofushi, Tokyo (JP); Mari Gotoh, Tokyo (JP); Kei Maruyama, Tokyo (JP); Keisuke Yoshikawa, Saitama (JP); Shinji Yamamoto, Saitama (JP)

(73) Assignees: OCHANOMIZU UNIVERSITY, Tokyo (JP); SAITAMA MEDICAL UNIVERSITY, Saitama (JP)

( * ) Notice: Subject to any disclaimer, the term of this patent is extended or adjusted under 35 U.S.C. 154(b) by 0 days.

(21) Appl. No.: 14/763,618

(22) PCT Filed: Jan. 28, 2014

(86) PCT No.: PCT/JP2014/051748
§ 371 (c)(1),
(2) Date: Jul. 27, 2015

(87) PCT Pub. No.: WO2014/115885
PCT Pub. Date: Jul. 31, 2014

(65) Prior Publication Data
US 2015/0352132 A1 Dec. 10, 2015

(30) Foreign Application Priority Data
Jan. 28, 2013 (JP) .................................. 2013-012859

(51) Int. Cl.
*A61K 31/665* (2006.01)
*A61K 31/67* (2006.01)
(Continued)

(52) U.S. Cl.
CPC .................................. *A61K 31/662* (2013.01)

(58) Field of Classification Search
CPC .............. C07F 9/6571; C07F 9/657109; C07F 9/657163
(Continued)

(56) References Cited

U.S. PATENT DOCUMENTS 6,150,345 A    11/2000    Chun et al.
6,914,056 B1    7/2005    Shinitzky
(Continued)

FOREIGN PATENT DOCUMENTS

EP    1 386 612    2/2004
JP    2002-308778    10/2002
(Continued)

OTHER PUBLICATIONS

Fujiwara "Cyclic phosphatidic Acid—A unique bioactive phospholipid," Biochim Biophys Acta, 2008, vol. 1781, No. 9, pp. 519-524 (NIH-PA Author Manuscript).*
(Continued)

*Primary Examiner* — Shengjun Wang
(74) *Attorney, Agent, or Firm* — Greenblum & Bernstein, P.L.C.

(57) ABSTRACT

It is an object of the present invention to provide a novel therapeutic agent for demyelinating disease which has an action to suppress demyelination of nerve axons. According to the present invention, a therapeutic agent for demyelinating disease which comprises cyclic phosphatidic acids, carba-cyclic phosphatidic acids, thia-cyclic phosphatidic acids, or a salt thereof is provided.

6 Claims, 5 Drawing Sheets

Specification includes a Sequence Listing.

(51) Int. Cl.
    *A61K 31/66*    (2006.01)
    *A61K 31/662*   (2006.01)
(58) Field of Classification Search
    USPC .................................. 514/99, 101, 110, 98
    See application file for complete search history.

(56) References Cited

U.S. PATENT DOCUMENTS

| 8,017,597 | B2 | 9/2011 | Murofushi et al. |
| 2004/0176329 | A1 | 9/2004 | Murofushi et al. |
| 2004/0214799 | A1 | 10/2004 | Mukai et al. |
| 2004/0220149 | A1 | 11/2004 | Murofushi et al. |
| 2009/0326256 | A1 | 12/2009 | Murofushi et al. |
| 2013/0281409 | A1 | 10/2013 | Steinman et al. |

FOREIGN PATENT DOCUMENTS

| JP | 2002-308779 | | 10/2002 | |
| JP | WO 2011065480 | A1 * | 6/2011 | ........... A61K 31/662 |
| JP | 2012-56853 | | 3/2012 | |
| WO | 00/09139 | | 2/2000 | |
| WO | 00/57865 | | 10/2000 | |
| WO | 2002/094286 | | 11/2002 | |
| WO | 2008/081580 | | 7/2008 | |
| WO | 2011/065480 | | 6/2011 | |
| WO | WO 2011151461 | A2 * | 12/2011 | ........... A61K 31/047 |

OTHER PUBLICATIONS

Mitew et al. "Focal demyelination in Alzheimer's disease and transgenic mouse models," Acta Neuropathol, 2010, vol. 119, pp. 567-577.*
WO2011065480A1 English translation.*
Baker et al. "Carba analogs of cyclic phosphatidic acid are selective inhibitor of autotaxin and cancer cell invasion and metastasis," J. Biol. Chem. 2006, vol. 281, No. 32. pp. 22786-22793.*
Dutta et al. "Mitochondrial Dysfunciton as a Cause of Axonal degeneration in Multiple Sclerosis Patients," Annals of Neurology, 2006, vol. 59, No. 3, pp. 478-489.*
Nozaki et al., "Pharmacological Evaluation of a Novel Cyclic Phosphatidic Acid Derivative 3-S-cyclic Phosphatidic Acid (3-S-cPA)", *Bioorganic & Medicinal Chemistry*, vol. 20, pp. 3196-3201, 2012.
Ho et al., "Identification of Naturally Occurring Fatty Acids of the Myelin Sheath that Resolve Neuroinflammation", *Science Translational Medicine*, 2012, vol. 4, No. 137, p. 137ra73, (Abstract) STN CAPLUS (online) Accession No. 2013:90360 (retrieved on Apr. 9, 2014).
Murakami-Murofushi et al., "Inhibition of Eukaryotic DNA Polymerase α with a Novel Lysophosphatidic Acid (PHYLPA) Isolated from Myxoamoebae of *Physarum polycephalum*", *The Journal of Biological Chemistry*, vol. 267, No. 30, pp. 21512-21517, 1992.
Matsushima et al., "The Neurotoxicant, Cuprizone, as a Model to Study Demyelination and Remyelination in the Central Nervous System", *Brain Pathology*, vol. 11, pp. 107-116, 2001.
Yoshikawa et al., "Inhibition of 5-Lipoxygenase Activity in Mice During Cuprizone-Induced Demyelination Attenuates Neuroinflammation, Motor Dysfunction and Axonal Damage", *Prostaglandins, Leukotrienes and Essential Fatty Acids*, vol. 85, pp. 43-52, 2011.
Torkildsen et al., "The Cuprizone Model for Demyelination", *Acta Neurol. Scand.*, vol. 117, pp. 72-76, 2008.
Uchiyama et al., "Inhibition of Transcellular Tumor Cell Migration and Metastasis by Novel Carba-Derivatives of Cyclic Phosphatidic Acid", *Biochimica et Biophysica Acta*, vol. 1771, pp. 103-112, 2007.
The Pharmaceutical Society of Japan, "Synthesis of Cyclic Phosphatidic Acid and Carba Derivatives and Physiological Action Thereof", 23rd Symposium on Progress in Organic Reactions and Syntheses (Citizens Hall Kumamoto), pp. 101-104 (Abstracts), Nov. 17-18, 1997.
Tanaka et al., "Efficient Synthesis of 3-O-thia-cPA and Preliminary Analysis of its Biological Activity Toward Autotaxin", *Bioorganic & Medicinal Chemistry Letters*, vol. 21, pp. 4180-4182, 2011.
Kobayashi et al., "Synthesis of 1-O-Acylglycerol 2,3-Cyclic Phosphate: Determination of the Absolute Structure of PHYLPA, a Specific Inhibitor of DNA Polymerase α", *Tetrahedron Letters*, vol. 34, No. 25, pp. 4047-4050, 1993.
International Search Report issued in PCT/JP2014/051748, dated May 13, 2014.
International Preliminary Report on Patentability issued in PCT/JP2014/051748, dated Jul. 30, 2015, along with an English translation.
Extended European Search Report issued in EP Patent Application No. 147431614.3, dated Jun. 22, 2016.
Sano et al., The Effect of cPA on Differentiation and Survival of Primary Culture of Oligodedrocytes, and Astrocytes, Cell Structure and Function, Japan Society for Cell Biology (JSCB), vol. 27, No. 4, p. 261, Aug. 1, 2002.
European Office Action issued with respect to Application No. 14743161.3, dated Oct. 26, 2017.

\* cited by examiner

[Figure 1]
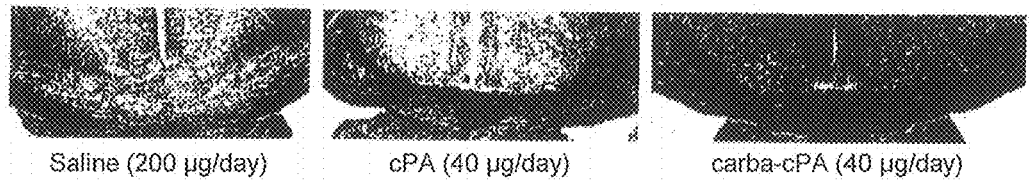
Saline (200 μg/day)    cPA (40 μg/day)    carba-cPA (40 μg/day)
[Figure 2]
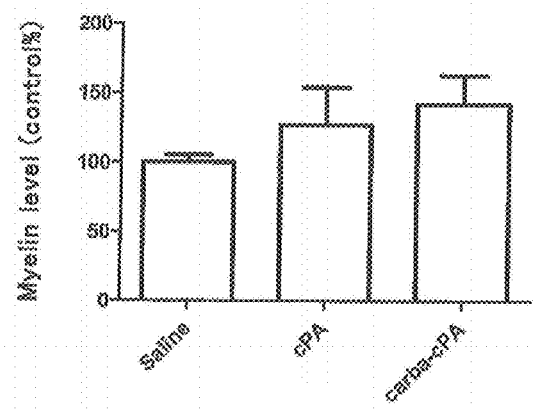
[Figure 3]
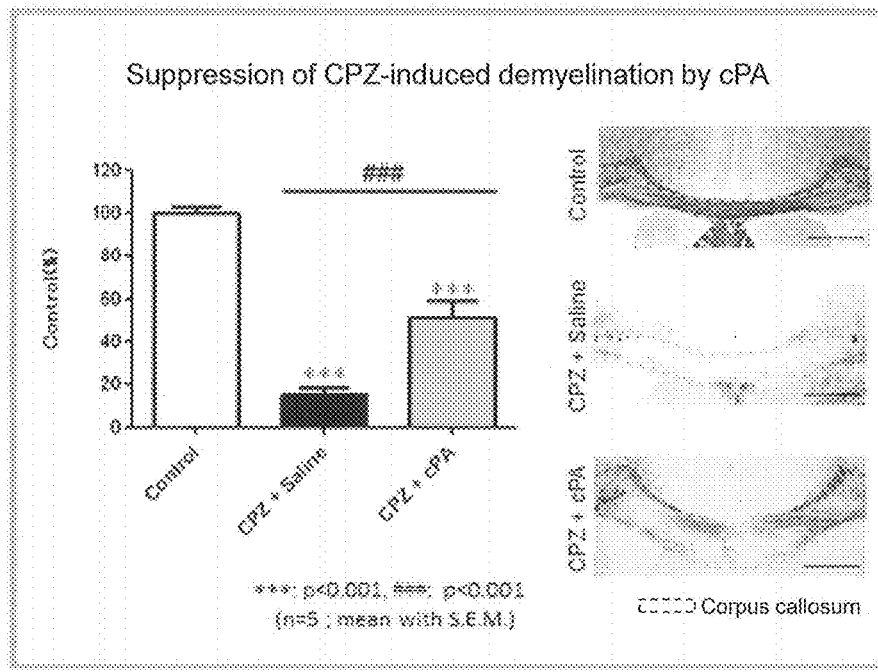

[Figure 4]
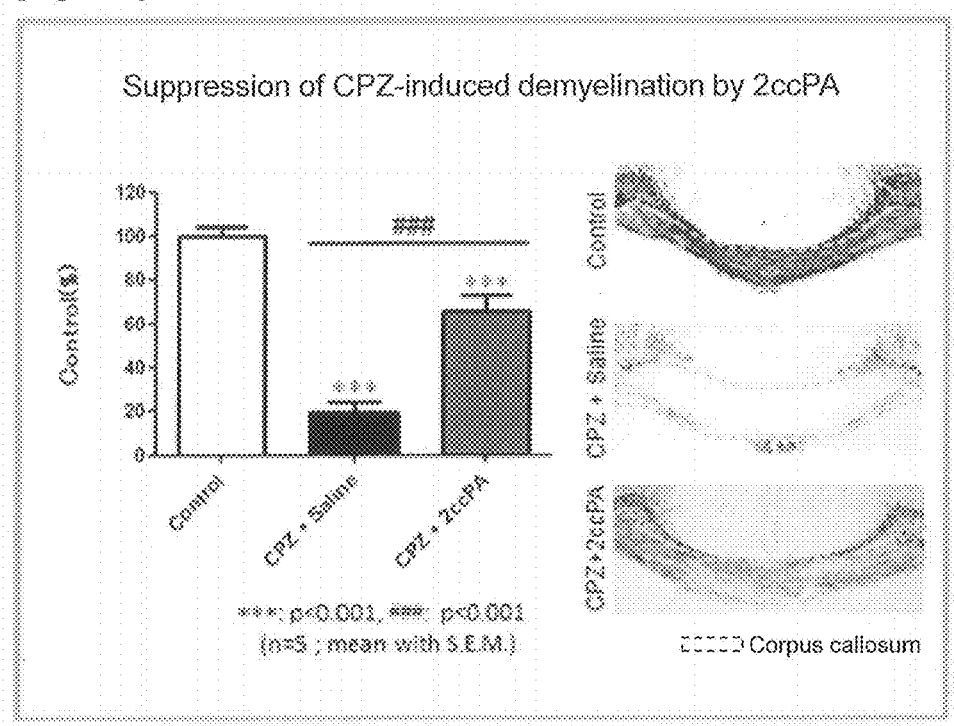
[Figure 5]
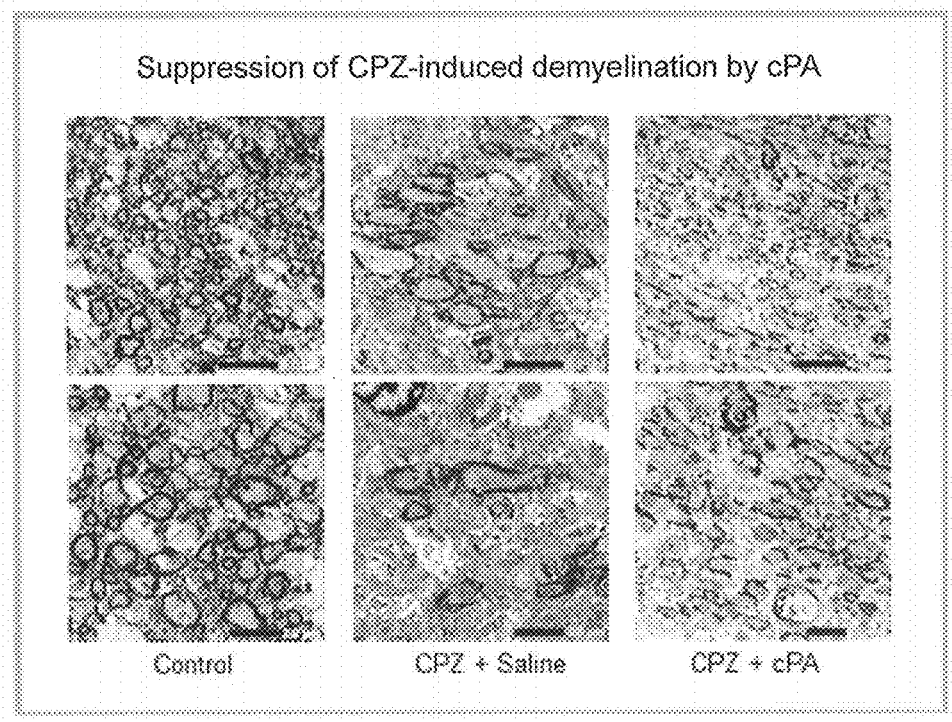

[Figure 6]
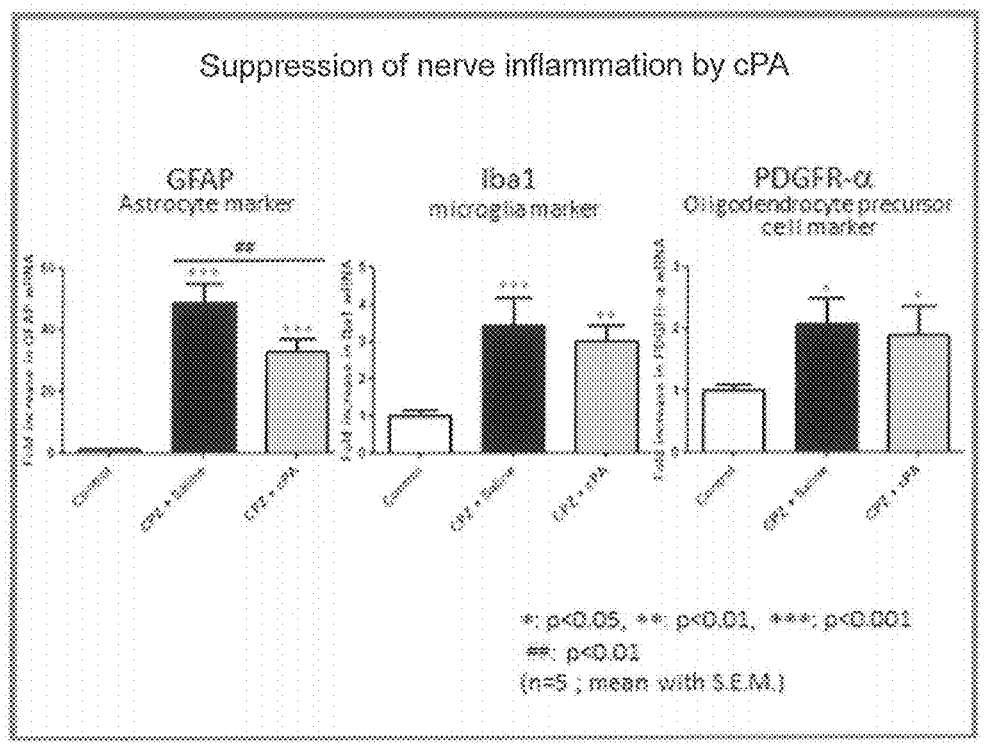
[Figure 7]
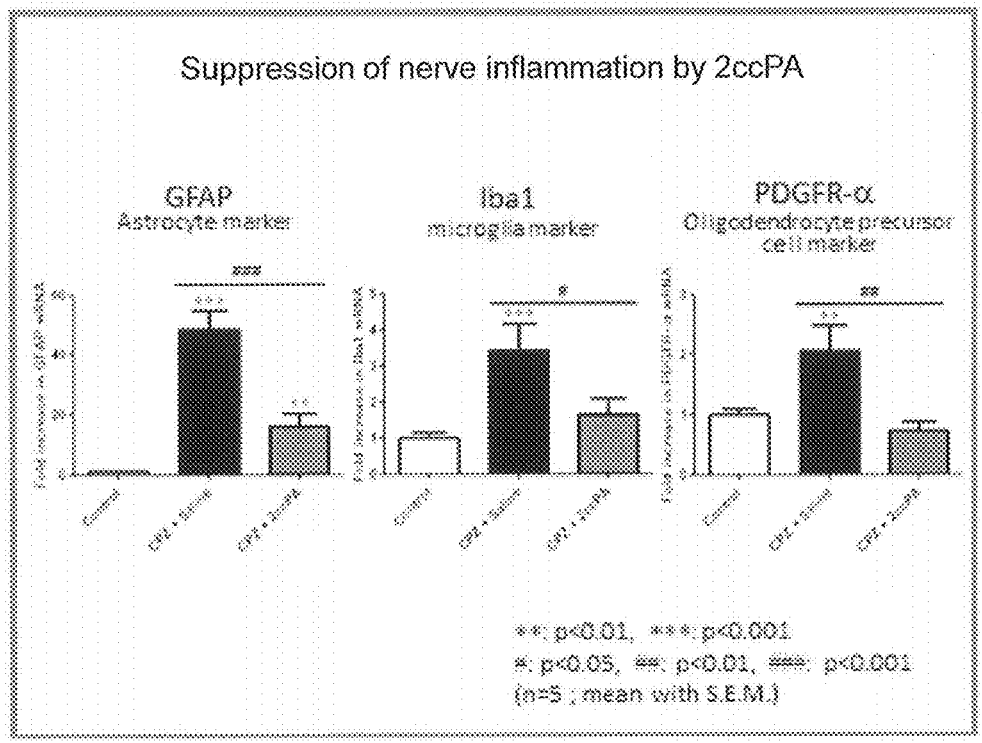

[Figure 8]
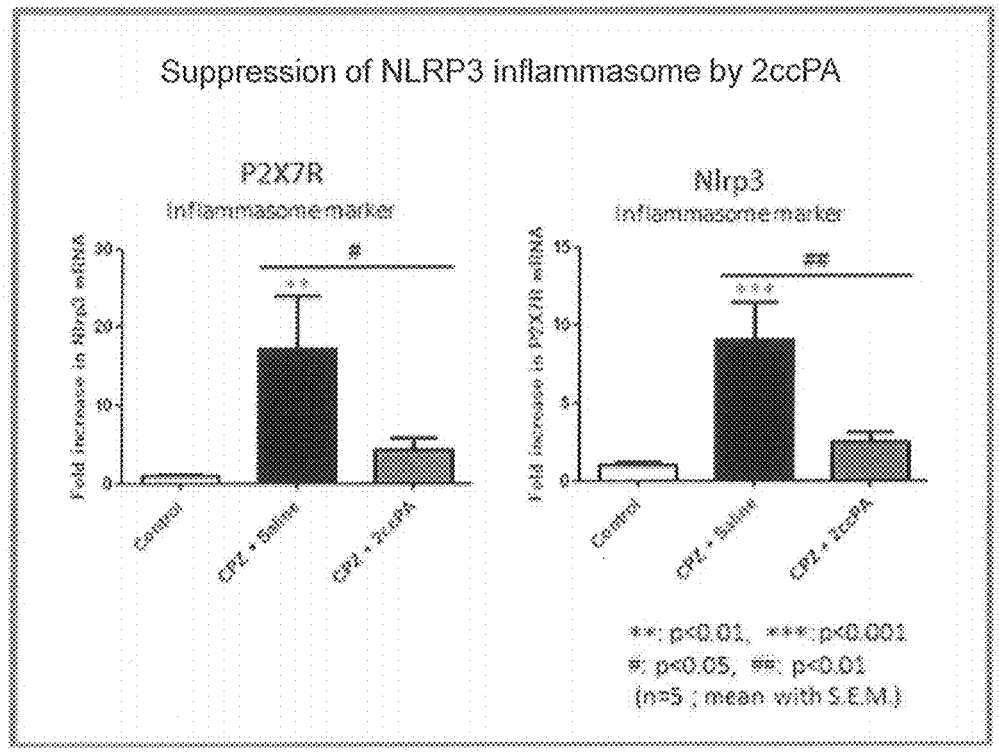
[Figure 9]
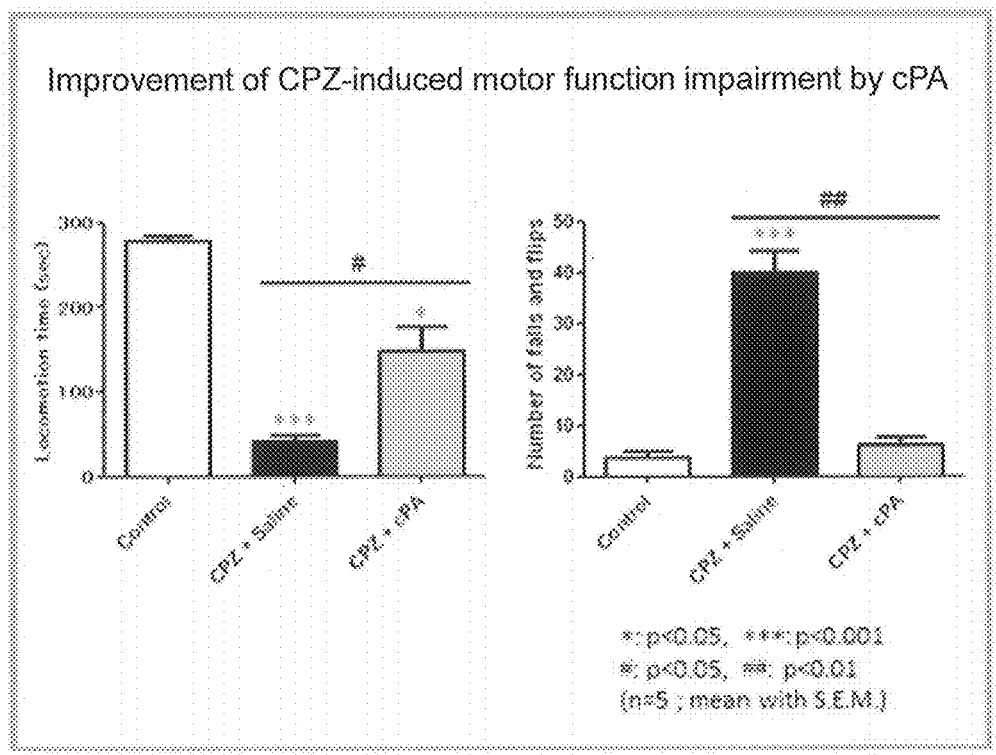

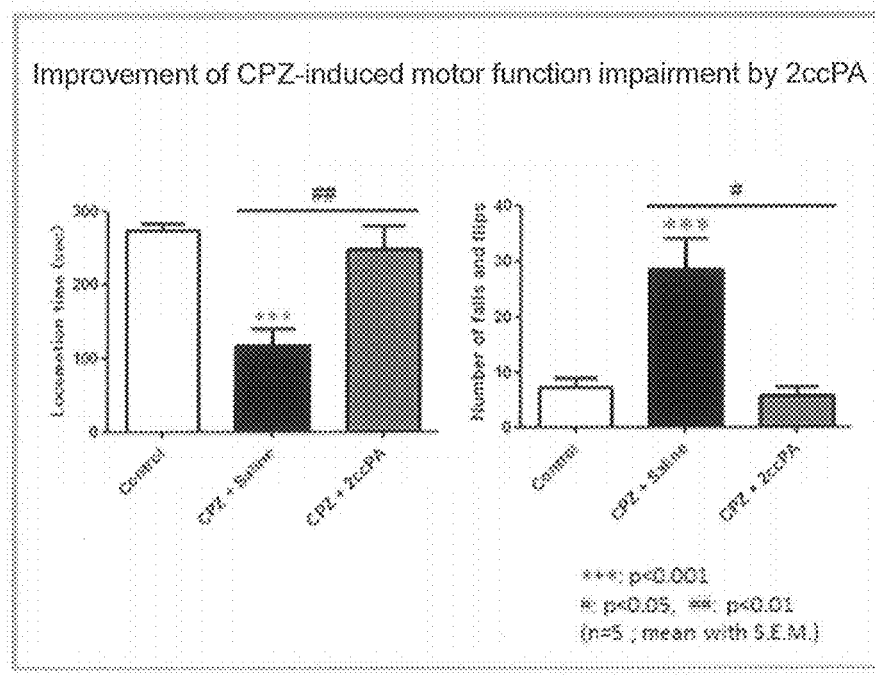
[Figure 10]

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgctgttcc aagcatcaaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
gcatcttttc ccttcccttc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgcttctcc ttgtctcgaa                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggcgatagt cgttagcttc                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgagccaaa gcagggattt                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaccagttgg cctcttgtgt                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caacagtggc ctctttgtca                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ctcccgttat tgtgcaaggt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtgtgcatt gacttgctca                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttgcagact tttcccaagc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttggacca ggttcagtgt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aggagatgtc gaagcagcat                                              20
```

METHOD FOR TREATING DEMYELINATING DISEASE

TECHNICAL FIELD

The present invention relates to a therapeutic agent for demyelinating disease comprising, as an active ingredient, cyclic phosphatidic acids, carba-cyclic phosphatidic acids or thia-cyclic phosphatidic acids, and an agent for suppressing demyelination of nerve axons comprising, as an active ingredient, cyclic phosphatidic acids, carba-cyclic phosphatidic acids or thia-cyclic phosphatidic acids.

BACKGROUND ART

A nerve fiber is composed of an axon passing through the center of the fiber and a myelin sheath surrounding the outside thereof. A major component of the myelin sheath is a lipid, and it is involved in a mechanism of promoting the electrical conduction of the nerve. Demyelinating disease is one type of neurological disease, which is developed when the myelin sheath is destroyed (demyelination change). This disease is caused by a viral infection, poisoning by alcohol and the like, malnutrition, etc. However, some demyelinating diseases are developed by an unknown cause (idiopathic demyelination). It has been assumed that the demyelinating disease would be developed by immune abnormality such as allergy or autoimmunization. In the demyelinating disease, a variety of symptoms such as movement disorders and sensory disorders in eyes, face, mouth, tongue, throat, hands and feet, and rectum and/or bladder disorders, appear as complicated and entangled elements. The demyelinating disease includes a central demyelinating disease and a peripheral demyelinating disease. Examples of the central demyelinating disease include multiple sclerosis (neuromyelitis optica (Devic syndrome) and concentric sclerosis (Balo's disease)), acute disseminated encephalomyelitis, inflammatory diffuse sclerosis (Schilder's disease), subacute sclerosis panencephalitis, progressive multifocal leukoencephalopathy, cerebral hypoxia, central pontine myelinolysis, vitamin B12 deficiency, and Binswanger's disease. Examples of the peripheral demyelinating disease include Guillain-Barre syndrome and chronic inflammatory demyelinating polyneuropathy.

On the other hand, in 1992, from haploid myxamoebae of *Physarum polycephalum*, a lipid-soluble substance, which is capable of suppressing the activity of DNA polymerase α that is a DNA polymerase enzyme for eukaryotic cells and suppressing proliferation of cultured animal cells, has been discovered and has been then isolated and purified (Murakami-Murofushi, K., et al., J. Biol. Chem. 267, 21512-21517 (1992)). This substance has been found to be a substance in which hexadecanoic acid containing cyclopropane binds to the sn-1 position of the glycerol backbone and phosphoric acid binds to each of the sn-2 and sn-3 positions via a cyclic ester bond. Since this substance is an LPA-like substance derived from *Physarum*, it has been named as "PHYLPA." PHYLPA has a characteristic fatty acid chain in the sn-1 position. Thus, a derivative in which the characteristic fatty acid chain was replaced with a general fatty acid chain, was chemically synthesized, and the activity thereof was then examined. As a result, it was demonstrated that the derivative suppresses cell proliferation, and thus, it was revealed that the proliferation-suppressing action of PHYLPA is caused by the cyclic phosphate groups in the sn-2 and sn-3 positions. At present, LPA analogs having such cyclic phosphate groups are collectively referred to as a "cyclic phosphatidic acid (cPA)."

[Formula 1]

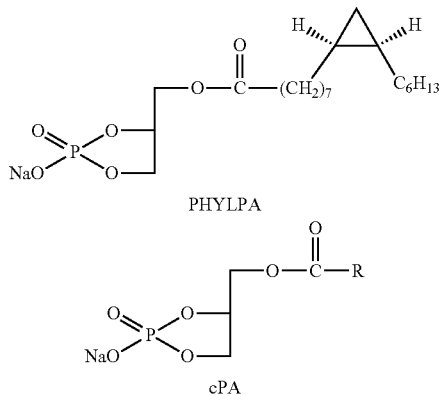

With regard to the cyclic phosphatidic acids and their derivatives, there have been several reports regarding an action as a neurotrophic factor and application thereof to neurodegenerative diseases (Patent Literatures 1 and 2), suppression of the proliferation, invasion and/or metastasis of cancer cells (Patent Literature 3), analgesic action (Patent Literature 4), and application to atopic dermatitis (Patent Literature 5). However, there have been no findings regarding the influence of the cyclic phosphatidic acid and their derivatives on demyelination of nerve axons.

PRIOR ART LITERATURE

Patent Literature

Patent Literature 1: JP Patent Publication (Kokai) No. 2002-308778
Patent Literature 2: JP Patent Publication (Kokai) No. 2002-308779
Patent Literature 3: International Publication WO 2002/94286
Patent Literature 4: International Publication WO 2008/81580
Patent Literature 5: JP Patent Publication (Kokai) No. 2012-56853

Non Patent Literature

Non Patent Literature 1: Murakami-Murofushi, K., et al., J. Biol. Chem. 267, 21512-21517 (1992)

DISCLOSURE OF INVENTION

Object to be Solved by the Invention

If a drug having an action to suppress demyelination of nerve axons were discovered, it would be possible to develop a novel therapeutic agent for demyelinating disease. It is an object of the present invention to provide a novel therapeutic agent for demyelinating disease which has an action to suppress demyelination of nerve axons.

Means for Solving the Object

The present inventors have found that cyclic phosphatidic acids, carba-cyclic phosphatidic acids, thia-cyclic phosphatidic acids, and their derivatives have an action to suppress demyelination of nerve axons, thereby completing the present invention.

Namely, the present invention provides a therapeutic agent for demyelinating disease which comprises cyclic phosphatidic acids, carba-cyclic phosphatidic acids, thia-cyclic phosphatidic acids, or salt thereof.

Another aspect of the present invention provides an agent for suppressing demyelination of nerve axons, which comprises cyclic phosphatidic acids, carba-cyclic phosphatidic acids, thia-cyclic phosphatidic acids, or salt thereof.

Preferably, the cyclic phosphatidic acids, carba-cyclic phosphatidic acids, or thia-cyclic phosphatidic acids are a compound represented by the following Formula (1):

[Formula 2]

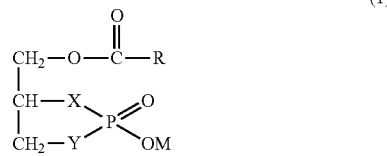

(1)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may optionally contain a cycloalkane ring or an aromatic ring; X and Y each independently represent —O—, —S— or —CH$_2$—, wherein X and Y do not simultaneously represent —CH$_2$—; and M represents a hydrogen atom or a counter cation.

Preferably, in the Formula (1), X and Y represent —O—.

Preferably, in the Formula (1), X represents —CH$_2$— and Y represents —O—.

Preferably, in the Formula (1), X represents —O— and Y represents —CH$_2$—.

Preferably, the compound represented by the Formula (1) is 1-oleoyl cyclic phosphatidic acid or 1-palmitoleoyl cyclic phosphatidic acid.

Preferably, the demyelinating disease is a central demyelinating disease, and is more preferably multiple sclerosis.

Preferably, the therapeutic agent for demyelinating disease according to the present invention is used as an agent for suppressing demyelination of nerve axons.

The present invention further provides a method for treating demyelinating disease, which comprises administering cyclic phosphatidic acids, carba-cyclic phosphatidic acids, thia-cyclic phosphatidic acids, or salt thereof to a patient suffering from demyelinating disease.

The present invention further provides a method for suppressing demyelination of nerve axons, which comprises administering cyclic phosphatidic acids, carba-cyclic phosphatidic acids, thia-cyclic phosphatidic acids, or salt thereof to a patient suffering from demyelinating disease.

The present invention further provides a use of cyclic phosphatidic acids, carba-cyclic phosphatidic acids, thia-cyclic phosphatidic acids, or salt thereof for production of a therapeutic agent for demyelinating disease.

The present invention further provides a use of cyclic phosphatidic acid, carba-cyclic phosphatidic acid, thia-cyclic phosphatidic acid, or salt thereof for production of an agent for suppressing demyelination of nerve axons, Advantageous Effects of Invention According to the present invention, a therapeutic agent for demyelinating disease and an agent for suppressing demyelination of nerve axons, which are characterized in that these agents comprise, as an active ingredient, cyclic phosphatidic acids, carba-cyclic phosphatidic acids, or thia-cyclic phosphatidic acids, can be provided.

BRIEF DESCRIPTION OF DRAWINGS

FIG. 1 shows the results obtained by subjecting mice administered with a test compound or a saline to perfusion fixation with 4% paraformaldehyde, and then preparing sections used for frozen tissue staining in a cryostat.

FIG. 2 shows the results obtained by measuring the level of myelin in mice administered with a test compound or a saline according to Black Gold staining.

FIG. 3 shows the tissue staining of the corpus callosum and evaluation of demyelination, in a case where the mice were administered with cPA.

FIG. 4 shows the tissue staining of the corpus callosum and evaluation of demyelination, in a case where the mice were administered with 2 ccPA.

FIG. 5 shows the results of electron microscope observation.

FIG. 6 shows genetic analysis by Q-PCR, in the case of administration of cPA.

FIG. 7 shows genetic analysis by Q-PCR, in the case of administration of 2 ccPA.

FIG. 8 shows genetic analysis by Q-PCR, in the case of administration of 2 ccPA.

FIG. 9 shows the results of a test of motor function impairment using a rotarod, in the case of administration of cPA.

FIG. 10 shows the results of a test of motor function impairment using a rotarod, in the case of administration of 2 ccPA.

EMBODIMENTS FOR CARRYING OUT THE INVENTION

Hereinafter, the present invention will be more specifically described.

The present invention relates to a therapeutic agent for demyelinating disease and an agent for suppressing demyelination of nerve axons (which are hereinafter referred to as "the drug of the present invention," at times), both of which comprise, as an active ingredient, a cyclic phosphatidic acid, a carba-cyclic phosphatidic acid, a thia-cyclic phosphatidic acid, or salt thereof. Specifically, the drug of the present invention can be used for the treatment of demyelinating disease, or suppression of demyelination of nerve axons, and it comprises, as an active ingredient, a cyclic phosphatidic acid, a carba-cyclic phosphatidic acid, a thia-cyclic phosphatidic acid, or salt thereof. The type of the cyclic phosphatidic acids, carba-cyclic phosphatidic acids, or thia-cyclic phosphatidic acids is not particularly limited, as long as it exhibits the effects of the present invention. The cyclic phosphatidic acids represented by the following Formula (I) can be preferably used.

[Formula 3]

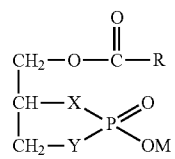

(1)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may optionally contain a cycloalkane ring or an aromatic ring; X and Y each independently represent —O—, —S— or —CH$_2$—, wherein X and Y do not simultaneously represent —CH$_2$—; and M represents a hydrogen atom or a counter cation.

Specific examples of the linear or branched alkyl group containing 1 to 30 carbon atoms, which is represented by the substituent R in the Formula (I), include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

Specific examples of the linear or branched alkenyl group containing 2 to 30 carbon atoms, which is represented by the substituent R, include an allyl group, a butenyl group, an octenyl group, a decenyl group, a dodecadienyl group, and a hexadecatrienyl group. More specific examples include a 8-decenyl group, a 8-undecenyl group, a 8-dodecenyl group, a 8-tridecenyl group, a 8-tetradecenyl group, a 8-pentadecenyl group, a 8-hexadecenyl group, a 8-heptadecenyl group, a 8-octadecenyl group, a 8-icosenyl group, a 8-docosenyl group, a heptadeca-8,11-dienyl group, a heptadeca-8,11,14-trienyl group, a nonadeca-4,7,10,13-tetraenyl group, a nonadeca-4,7,10,13,16-pentaenyl group, and a henicosa-3,6,9,12,15,18-hexaenyl group.

Specific examples of the linear or branched alkynyl group containing 2 to 30 carbon atoms, which is represented by the substituent R, include a 8-decynyl group, a 8-undecynyl group, a 8-dodecynyl group, a 8-tridecynyl group, a 8-tetradecynyl group, a 8-pentadecynyl group, a 8-hexadecynyl group, a 8-heptadecynyl group, a 8-octadecynyl group, a 8-icosynyl group, a 8-docosynyl group, and a heptadeca-8,11-diynyl group.

Specific examples of a cycloalkane ring, which may be optionally comprised in the above described alkyl group, alkenyl group or alkynyl group, include a cyclopropane ring, a cyclobutane ring, a cyclopentane ring, a cyclohexane ring, and a cyclooctane ring. The cycloalkane ring may comprise one or more heteroatoms, and examples of such a cycloalkane ring include an oxirane ring, an oxetane ring, a tetrahydrofuran ring, and an N-methylprolidine ring.

Specific examples of an aromatic ring, which may be optionally comprised in the above described alkyl group, alkenyl group or alkynyl group, include a benzene ring, a naphthalene ring, a pyridine ring, a furan ring, and a thiophene ring.

Accordingly, specific examples of the substituent R that is an alkyl group substituted with a cycloalkane ring include a cyclopropylmethyl group, a cyclohexylethyl group, and a 8,9-methanopentadecyl group.

Specific examples of the substituent R that is an alkyl group substituted with an aromatic ring include a benzyl group, a phenethyl group, and a p-pentylphenyl octyl group.

R preferably represents a linear or branched alkyl group containing 9 to 17 carbon atoms, a linear or branched alkenyl group containing 9 to 17 carbon atoms, or a linear or branched alkynyl group containing 9 to 17 carbon atoms. R more preferably represents a linear or branched alkyl group containing 9, 11, 13, 15 or 17 carbon atoms, or a linear or branched alkenyl group containing 9, 11, 13, 15 or 17 carbon atoms. R particularly preferably represents a linear or branched alkenyl group containing 9, 11, 13, 15 or 17 carbon atoms.

X and Y in the compound represented by the general formula (1) each independently represent —O—, —S— or —CH$_2$—. However, X and Y do not simultaneously represent —CH$_2$—. That is to say, there are the following three combinations of X and Y.
(1) X represents —O—, and Y also represents —O—.
(2) X represents —CH$_2$—, and Y represents —O— (2-carba-cPA (which is also abbreviated as "2 ccPA")). Otherwise, X represents —S—, and Y represents —O—.
(3) X represents —O—, and Y represents —CH$_2$— (3-carba-cPA (which is also abbreviated as "3 ccPA")). Otherwise, X represents —O—, and Y represents —S—.

Among the aforementioned combinations, particularly preferably, X represents —CH$_2$—, and Y represents —O— (2-carba-cPA).

M in the cyclic phosphatidic acid derivative represented by the Formula (I) represents a hydrogen atom or a counter cation. Examples of M that is a counter cation include an alkali metal atom, an alkaline-earth metal atom, and a substituted or unsubstituted ammonium group. Examples of the alkali metal atom include lithium, sodium, and potassium, and examples of the alkaline-earth metal atom include magnesium and calcium. Examples of the substituted ammonium group include a butylammonium group, a triethylammonium group, and a tetramethylammonium group.

The compound of the Formula (I) may include isomers such as a position isomer, a geometric isomer, a tautomer or an optical isomer, depending on the type of the substituent. All possible isomers and mixtures comprising two or more types of such isomers at any given ratio are included in the scope of the present invention.

Moreover, the compound of the Formula (I) may be present in the form of an adduct with water or various types of solvents (a hydrate or a solvate). These adducts are also included in the scope of the present invention. Furthermore, any given crystalline forms of the compound of the Formula (I) and a salt thereof are also included in the scope of the present invention.

The compound represented by the Formula (1) is preferably 1-oleoyl cyclic phosphatidic acid or 1-palmitoleoyl cyclic phosphatidic acid. Specific examples of the compound represented by the Formula (1) used in the present invention include oleoyl 2-carba-cPA (ΔOle-2 ccPA) and palmitoleoyl 2-carba-cPA (ΔPal-2 ccPA).

The compound represented by the formula (1), wherein X and Y represent —O—, can be chemically synthesized in accordance with the methods described in, for example, Kobayashi, S., et al.: Tetrahedron Lett., 34, 4047-4050 (1993), JP Patent Publication (Kokai) No. 5-230088 (1993), JP Patent Publication (Kokai) No. 7-149772 (1995), JP Patent Publication (Kokai) No. 7-258278 (1995), and JP Patent Publication (Kokai) No. 9-25235 (1997).

Moreover, the compound represented by the formula (1), wherein X and Y represent —O—, can also be synthesized by phospholipase D treatment to act on lysophospholipids in accordance with the method described in JP Patent Publication (Kokai) No. 2001-178489. The type of lysophospholipids used herein is not particularly limited, as long as they are lysophospholipids on which phospholipase D is functioned. Many types of lysophospholipids have been known, and specifically, lysophospholipids having different types of fatty acid chains, lysophospholipids having an ether or vinylether bond, and the like have been known. These lysophospholipids can be obtained as commercially available products. As phospholipase D, those derived from higher vegetables such as cabbage or peanuts, and those derived from microorganisms such as *Streptomyces chromofuscus* or *Actinomadula* sp. can be obtained as commercially available reagents. By the enzyme derived from *Actinomadula* sp. No. 362, cPA is extremely selectively synthesized (JP Patent Publication (Kokai) No. 11-367032 (1999), specification). The reaction of lysophospholipids with phospholipase D is not particularly limited, as long as it is carried out under conditions in which the enzyme can exhibit its activity. For example, the reaction is carried out in an acetate buffer containing calcium chloride (approximately pH 5 to 6) at room temperature or under warming (preferably, approximately 37° C.) for about 1 to 5 hours. The generated cPA derivatives can be purified by extraction, column chromatography, thin-layer chromatography (TLC), etc., in accordance with ordinary methods.

Furthermore, the compound represented by the formula (1), wherein X or Y represents —S—, can be synthesized in accordance with the descriptions of Bioorganic & Medicinal Chemistry Letters 21 (2011) 4180-4182, or Bioorganic & Medicinal Chemistry 20 (2012) 3196-3201.

Further, the compound represented by the formula (1), wherein X represents —CH$_2$— and Y represents —O—, can be synthesized according to the method described in JP Patent Publication (Kokai) No. 2004-010582 or International Publication WO 03/104246.

Still further, the compound represented by the formula (1), wherein X represents —O— and Y represents —CH$_2$—, can be synthesized in accordance with the methods described in publications (Uchiyama A. et al., Biochimica et Biophysica Acta 1771 (2007) 103-112; and the Pharmaceutical Society of Japan, the 23rd Symposium regarding the Progress of Reaction and Synthesis, Nov. 17-18, 1997, (Citizens Hall Kumamoto), "Synthesis of Cyclic Phosphatidic Acid and Carba Derivatives and Physiological Action Thereof," Abstracts pp. 101-104). Alternatively, this compound can be synthesized by the method described in International Publication WO 2002/094286. An example of the specific synthetic pathway will be shown below.

[Formula 4]

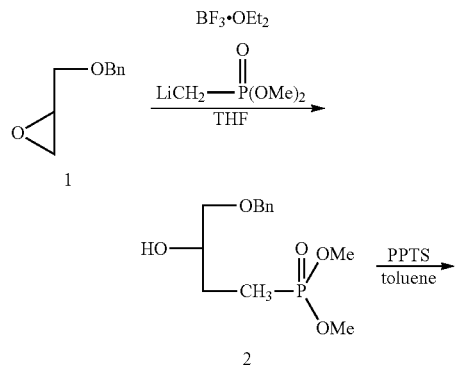

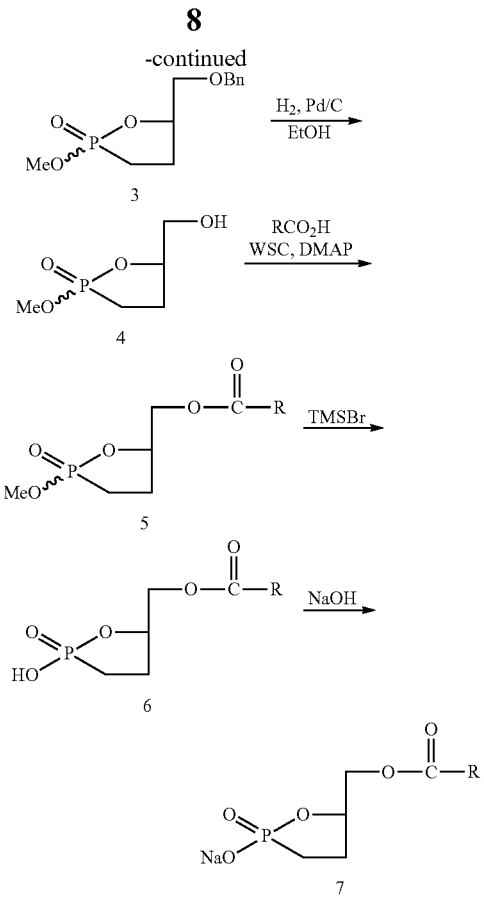

In the aforementioned pathway, first, a commercially available (R)-benzylglycidyl ether (1) is activated by BF$_3$.Et$_2$O, and the activated compound is then allowed to react with a lithiated form obtained by allowing n-BuLi to act on methylphosphonic acid dimethyl ester, so as to obtain alcohol (2).

The obtained alcohol is allowed to react with an excessive amount of pyridinium salt of p-toluenesulfonic acid in toluene at 80° C. to obtain a cyclized form (3). This cyclized form is hydrolyzed using 20% Pd(OH)$_2$—C in a hydrogen atmosphere to perform debenzylation (4). Using 1-ethyl-3-(3-dimethylaminopropyl)carbodiimide hydrochloride as a condensing agent, the compound (4) is allowed to react with fatty acid to obtain a coupled form (5). Subsequently, using bromotrimethylsilane as a nucleophilic agent, only the methyl group is removed in a regioselective manner to obtain a cyclic phosphonic acid (6). Using ether, this cyclic phosphonic acid is transferred into a reparatory funnel, and a small amount of 0.02 N sodium hydroxide aqueous solution is then added dropwise thereto to perform a liquid separation operation, so that a compound of interest is extracted and purified as a sodium salt (7).

Since the cyclic phosphatidic acids, carba-cyclic phosphatidic acids, thia-cyclic phosphatidic acids, or salt thereof, which is used as an active ingredient in the present invention, has an action to suppress demyelination of nerve axons, it can be used as a therapeutic agent for demyelinating disease or an agent for suppressing demyelination of nerve axons.

The demyelinating disease as an administration target of the drug of the present invention may be either a central demyelinating disease or a peripheral demyelinating disease. Examples of the central demyelinating disease include multiple sclerosis (neuromyelitis optica (Devic syndrome) and concentric sclerosis (Balo's disease)), acute disseminated encephalomyelitis, inflammatory diffuse sclerosis (Schilder's disease), sub-acute sclerosis panencephalitis, progressive multifocal leukoencephalopathy, cerebral hypoxia, central pontine myelinolysis, vitamin B12 deficiency, and Binswanger's disease. Examples of the peripheral demyelinating disease include Guillain-Barre syndrome and chronic inflammatory demyelinating polyneuropathy. Among these diseases, the drug of the present invention is particularly useful as a therapeutic agent for multiple sclerosis.

The drug of the present invention is preferably provided in the form of a pharmaceutical composition comprising one or two or more pharmaceutically acceptable additives, and a cyclic phosphatidic acids, a carba-cyclic phosphatidic acids or a thia-cyclic phosphatidic acids (preferably, the compound represented by the Formula (1)), or a salt thereof, which is as an active ingredient.

The drug of the present invention can be administered in various administration forms. A preferred administration form may be either oral administration or parenteral administration (e.g., intravenous, intramuscular, subcutaneous or intradermal injection, intrarectal administration, transmucosal administration, etc.). Examples of the pharmaceutical composition suitable for oral administration include a tablet, a granule, a capsule, a powder agent, a solution agent, a suspending agent, and syrup. Examples of the pharmaceutical composition suitable for parenteral administration include an injection, a drop, a suppository, and a transdermal absorption agent. However, the dosage form of the drug of the present invention is not limited thereto. Moreover, the drug of the present invention can also be processed into a deposit preparation according to a known technique. For instance, cyclic phosphatidic acids, carba-cyclic phosphatidic acids, thia-cyclic phosphatidic acids, or a salt thereof used as an active ingredient is encapsulated into hydrogel comprising gelatin as a base agent, so as to produce a sustained release preparation.

The type of a pharmaceutical additive used in the production of the drug of the present invention is not particularly limited, and it can be selected, as appropriate, by a person skilled in the art. Examples of the pharmaceutical additive that can be used herein include an excipient, a disintegrator or a disintegration aid, a binder, a lubricant, a coating agent, a base agent, a dissolving agent or a dissolution aid, a dispersant, a suspending agent, an emulsifier, a buffer agent, an antioxidant, an antiseptic, an isotonic agent, a pH adjuster, a solubilizer, and a stabilizer. Individual specific components used for these purposes have been well known to a person skilled in the art.

Examples of a pharmaceutical additive that can be used in the production of a preparation for oral administration include: excipients such as glucose, lactose, D-mannitol, starch or crystalline cellulose; disintegrators or disintegration aids, such as carboxymethyl cellulose, starch or carboxymethylcellulose calcium; binders such as hydroxypropyl cellulose, hydroxypropylmethyl cellulose, polyvinylpyrrolidone or gelatin; lubricants such as magnesium stearate or talc; coating agents such as hydroxypropylmethyl cellulose, saccharose, polyethylene glycol or titanium oxide; and base agents such as Vaseline, liquid paraffin, polyethylene glycol, gelatin, kaolin, glycerin, purified water or hard fat.

Examples of a pharmaceutical additive that can be used in the production of a preparation for injections or drops include: dissolving agents or dissolution aids that may constitute an aqueous or use-time dissolution type injection, such as distilled water for injection, a normal saline, propylene glycol or a surfactant; isotonic agents such as glucose, sodium chloride, D-mannitol or glycerin; and pH adjusters such as inorganic acid, organic acid, an inorganic base or an organic base.

The drug of the present invention can be administered to mammals such as humans.

The applied dose of the drug of the present invention should be increased or decreased, as appropriate, depending on the age, sex, or body weight of a patient, symptoms, an administration route, and the like. In general, the amount of the active ingredient of the present drug per adult per day is in the range of approximately from 1 µg/kg to 1,000 mg/kg, and preferably in the range of approximately from 10 µg/kg to 100 mg/kg. The aforementioned dose of drug may be administered once or divided over several administrations (e.g., about two to four times) per day.

Hereinafter, the present invention will be specifically described in the following examples. However, these examples are not intended to limit the scope of the present invention.

EXAMPLES

Example 1

(1) Test Compound

The cPA used in the experiment is cPA (16:0), and the carba-cPA is 2 ccPA (16:1).

The structure of the cPA (16:0) is as follows. In the formula shown below, $-C_{15}H_{31}$ indicates $-(CH_2)_{14}CH_3$. As the cPA (16:0), a chemically synthesized product that had been synthesized in accordance with the method described in Kobayashi, S., et al.: Tetrahedron Lett., 34, 4047-4050 (1993) was used.

[Formula 5]

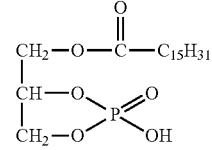

The structure of the 2 ccPA (16:1) is as follows. In the formula shown below, $-C_{15}H_{29}$ indicates $-(CH_2)_7CH=CH(CH_2)_5CH_3$ (a cis form). The 2 ccPA (16:1) was synthesized by the method described in JP Patent Publication (Kokai) No. 2004-010582.

[Formula 6]

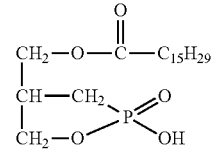

(2) Production of Demyelination Model Mice 10-week-old male C57BL/6 mice were fed with a mash feed containing 0.2% cuprizone for five weeks until the most significant demyelination occurred, so as to produce demyelination model mice.

(3) Method of Administering Test Compound cPA and carba-cPA (cPA) powders were each dissolved in a saline, and the obtained solutions were each administered intraperitoneally at a dose of 40 μg/200 μl saline/day to the mice every day for 5 weeks. On the other hand, to negative control mice, a saline (200 μl/day) was intraperitoneally administered in the same manner as described above.

(4) Evaluation of Demyelination

The mice, to which the test compound had been administered, were subjected to perfusion fixation with 4% paraformaldehyde, and sections to be used for frozen tissue staining (30 μm) were then prepared in a cryostat (FIG. 1). The level of myelin in each mouse was measured by Black Gold staining, and the demyelination level was then measured based on the stained level (FIG. 2).

From the results shown in FIG. 2, it was demonstrated that the level of myelin in a mouse, to which cPA or carba-cPA had been administered, was higher than the level of myelin in a control mouse, and thus that demyelination of nerve axons could be suppressed by administration of cPA or carba-cPA.

The fact that cuprizone model mice can be used as model mice for demyelinating diseases such as multiple sclerosis is described, for example, in O. Torkildsen et al., Acta Neurol Scand 2008: 117 (suppl. 188): 72-76; and Glenn K. Matsushima et al., Brain Pathology 11: 107-116 (2001). In addition, the fact that an action to suppress a decrease in the myelin level in cuprizone model mice is used to demonstrate therapeutic effects on demyelinating diseases is described, for example, in K. Yoshikawa et al., Prostaglandins, Leukotrienes and Essential Fatty Acids 85 (2011) 43-52 (in particular, FIG. 4 and FIGS. 5D and 5E).

Moreover, even in the case of using cPA (18:1) and 2 ccPA (18:1) having the following structures [wherein $-C_{17}H_{33}$ indicates $-(CH_2)_7CH=CH(CH_2)_7CH_3$ (a cis form)], the same results as in the case of cPA (16:0) and 2 ccPA (16:1) were obtained.

[Formula 7]

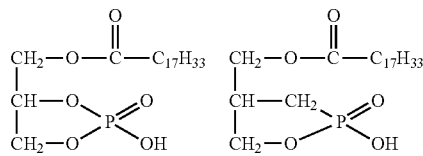

Example 2

(1) Method for Producing Experimental Animals and Multiple Sclerosis Models 10-week-old male C57BL/6j mice (Tokyo Laboratory Animals Science Co., Ltd., Tokyo, Japan) were fed by the discretionary intake of a mash feed (CLEA Japan, Inc.) that contained 0.2% cuprizone (biscyclohexanone oxalyl hydrazone; Merck KGaA, Darmstadt, Germany) for 5 weeks until demyelination progressed most, so as to produce demyelination model mice involving demyelination caused by oligodendrocyte-specific cell death.

To obtain mouse corpus callosum tissues to be used for genetic analysis, mouse brain was removed, and the corpus callosum tissues were then collected from the brain. Specifically, a site ranging from approximately −0.25 mm to −1.25 mm from the bregma was cut into a coronal plane, and further, tissues located in the upper and lower parts of the corpus callosum were removed by cutting them into a traverse plane, so as to recover the corpus callosum tissues. The recovered tissues were frozen by liquid nitrogen, and were then preserved at −80° C.

To obtain tissues to be used for histological analysis, a mouse was subjected to perfusion fixation through the heart with 4% paraformaldehyde, and the resulting brain tissues were then excised from the mouse. Thereafter, the tissues were immobilized and infiltrated with 30% sucrose. Thereafter, a frozen tissue block was prepared and was then sliced in a cryostat.

(2) Administration of cPA and 2 ccPA

The cPA used in the experiment was the same cPA (16:0) as that used in Example 1, and the carba-cPA was 2 ccPA (16:1). The cPA and 2 ccPA were chemically purified (Biochimica et Biophysica Acta, Emi Nozaki 2011), and were then dissolved in a 0.9% saline. The cPA and 2 ccPA were continuously administered to mice via intraperitoneal administration for 5 weeks (1.6 mg/kg/day), at the same time with administration of cuprizone. Control mice were fed with a normal mash feed, and a normal saline was continuously administered to the control mice via intraperitoneal administration for 5 weeks.

(3) Histological Staining of Corpus Callosum and Evaluation of Demyelination

A 20-μm section was produced as a site ranging from −0.22 mm to −0.58 from the bregma comprising the corpus callosum in a cryostat (LEICA CM1900, Wetzlar, Germany), and it was then recovered on a gelatin-coated slide glass. The section was stained with 0.3% Black Gold II (Histo-Chem, Jefferson, Ark.) at 65° C. for 12 minutes, and was then rinsed with sterilized water. Thereafter, 1% sodium thiosulfate was supplied through the section for 3 minutes, and the resulting section was subjected to dehydration and penetration. After that, it was mounted in Polymount (Polysciences Inc. Boston, Mass.). The stained section was photographed by KEYENCE BZ-9000, and then, using KEYENCE BZ-9000 Analyzer BZ-II Analyzer, the removal of the background and insertion of the scale bar were carried out. For the analysis of the level of myelin, using Image J 1.46r software, the stained level in the corpus callosum area was measured, and the demyelination level was then evaluated, while setting the control as 100%.

The results obtained in the case of administration of cPA are shown in FIG. 3. The results obtained in the case of administration of 2 ccPA are shown in FIG. 4. It was demonstrated that demyelination is suppressed by cPA and 2 ccPA.

(4) Electron Microscope

Five weeks after administration of cuprizone, mice were subjected to perfusion fixation with 4% paraformaldehyde, and the brain was then collected from each mouse. Thereafter, corpus callosum tissues were removed from the brain, were then pre-fixed with 2.5% glutaraldehyde fixative, and were then washed with a 0.1 M cacodylate buffer. After that, the tissues containing the corpus callosum were cut into a section with a size of approximately 1 mm, and it was then post-fixed with a 1% osmium fixative. Thereafter, dehydration and replacement with an epoxy resin using QY-1 were carried out, and the corpus callosum tissues were then embedded in a capsule, followed by polymerization at 56° C. With regard to the section, using a diamond knife, an ultrathin sliced section was prepared with an ultramicrotome Reichert-Nissei ULTRACUT-N (Nissei Sangyo, Tokyo, Japan), and was then stained with uranyl acetate. The section was photographed using a transmission electron microscope JEM-1400 Electron Microscope (JEOL Ltd, Tokyo, Japan), and the structure of myelin surrounding the nerve in the corpus callosum site was observed and was then photographed. The results are shown in FIG. 5. It was demonstrated that demyelination is suppressed by cPA.

(5) Genetic Analysis Using Q-PCR mRNA was extracted from the frozen corpus callosum tissues using ISOGEN (Nippon Gene Co., Ltd., Tokyo, Japan), was then dissolved in RNase free molecular grade water (Takara Bio Inc., Shiga, Japan), and was then preserved at −80° C. The mRNA was reverse-transcribed using Prime script RT reagent kit (Takara Bio Inc., Shiga, Japan). Gene expression was detected using 7900 Sequence Detection System (Applied Biosystems). The results of real-time PCR were obtained by making analysis using the expression level of phosphoglycerate kinase 1 (PGK1) as an internal control. For the analysis of gene expression, individual gene-specific primers were prepared, and measurement was then carried out (PGK-1; NM_008828 Forward: ctgctgttccaagcatcaaa Reverse: gcatatttccatcccttc); Glial Fibrillary Acidic Protein (GFAP; NM_001131020 Forward: acgcttctccttgtctcgaa Reverse: cggcgatagtcgttagcttc); Ionized calcium binding adapter molecule 1 (Iba1; D86382 Forward: atgagccaaagcagggattt Reverse: gaccagttggcctcttgtgt); Platelet Derived Growth Factor Receptor, alpha (PDGFRa; NM_011058 Forward caacagtggcctctttgtca Reverse ctcccgttattgtgcaaggt); Purinergic receptor P2X, ligand-gated ion channel, 7 (P2rx7; NM_011027 Forward tgtgtgcattgacttgctca Reverse cttgcagacttttcccaagc); and NLR family, pyrin domain containing 3 (Nlrp3; NM 145827.3 Forward ccttggaccaggttcagtgt Reverse aggagatgtcgaagcagcat). As conditions for Q-PCR, after completion of the initial denaturation for 30 seconds at 95° C., the reaction was carried out for 40 cycles each consisting of 5 seconds at 95° C. and 34 seconds at 60° C. The gene expression level was calculated by a $\Delta\Delta C_T$ method. Data were analyzed by a relative quantification method. A relative change in the gene expression was analyzed, while setting the gene expression level in a control mouse at 100%.

The results obtained in the case of administration of cPA are shown in FIG. 6. The results obtained in the case of administration of 2 ccPA are shown in FIG. 7 and FIG. 8. It was demonstrated that nerve inflammation is suppressed by cPA and 2 ccPA.

(6) Test of Motor Function Impairment Using Rotarod

A test of motor function impairment was carried out by measuring the motor function of mice 5 weeks after administration of cuprizone, using Rotarod Treadmill for mice (Muromachi Kikai, Co. Ltd., Tokyo, Japan). All mice were subjected to the experiment at 28 rpm. The locomotion time on the rod was evaluated by measuring the time required for the mice to fall from the rotating rod within a record time of 300 seconds. Moreover, even after the mice had fallen from the rod, they were forced to continue their activity immediately after the falling, so that a total number of the activities from falling from the rod to holding on to the rod for 300 seconds (a number of falls and flips) was measured and evaluated.

(7) Statistical Analysis

The data of the test of motor function impairment were analyzed according to a non-parametric method using a Kruskal-Wallis test. All of other data were analyzed according to a one-way ANOVA method using a Newman-Keulis test. Employing Graph Pad Prism Ver.5.01 software (Graph Pad Software, Inc., San Diego, Calif.), all the data were evaluated, using mean±SEM. p values <0.05 as a statistically significant difference.

The results obtained in the case of administration of cPA are shown in FIG. 9. The results obtained in the case of administration of 2 ccPA are shown in FIG. 10. It was demonstrated that motor function impairment is improved by cPA and 2 ccPA.

The invention claimed is:

1. A method for treating demyelinating disease, which comprises administering carba-cyclic phosphatidic acids or a salt thereof to a patient suffering from demyelinating disease, wherein:

the demyelinating disease is selected from the group consisting of multiple sclerosis, neuromyelitis optica (Devic syndrome), concentric sclerosis (Balo's disease), acute disseminated encephalomyelitis, inflammatory diffuse sclerosis (Schilder's disease), sub-acute sclerosis panencephalitis, progressive multifocal leukoencephalopathy, central pontine myelinolysis, vitamin B12 deficiency, Guillain-Barre syndrome, and chronic inflammatory demyelinating polyneuropathy, motor function impairment of the patient is improved, and the carba-cyclic phosphatidic acids are compounds represented by Formula (1):

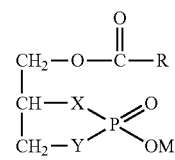

(1)

where:
R represents —(CH$_2$)$_7$CH═CH(CH$_2$)$_7$CH$_3$;
X represents —CH$_2$—;
Y represents —O—; and
M represents a hydrogen atom or a counter cation.

2. The method for treating demyelinating disease according to claim 1, wherein a demyelination of nerve axons is suppressed.

3. The method for treating demyelinating disease according to claim 1, wherein the carba-cyclic phosphatidic acid or a salt thereof is administered every day for 5 weeks.

4. A method for improving motor function impairment of a patient suffering from demyelinating disease, which comprises administering an effective amount of carba-cyclic phosphatidic acids or a salt thereof to the patient to improve motor function impairment of the patient, wherein:
the demyelinating disease is selected from the group consisting of multiple sclerosis, neuromyelitis optica (Devic syndrome), concentric sclerosis (Balo's disease), acute disseminated encephalomyelitis, inflammatory diffuse sclerosis (Schilder's disease), sub-acute sclerosis panencephalitis, progressive multifocal leukoencephalopathy, central pontine myelinolysis, vitamin B12 deficiency, Guillain-Barre syndrome, and chronic inflammatory demyelinating polyneuropathy, and the carba-cyclic phosphatidic acids are compounds represented by Formula (1):

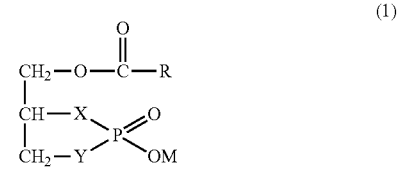

where:
R represents —(CH$_2$)$_7$CH═CH(CH$_2$)$_7$CH$_3$;
X represents —CH$_2$—;
Y represents —O—; and
M represents a hydrogen atom or a counter cation.

5. The method for improving motor function impairment of a patient suffering from demyelinating disease according to claim 4, wherein a demyelination of nerve axons is suppressed.

6. The method for improving motor function impairment of a patient suffering from demyelinating disease according to claim 4, wherein the carba-cyclic phosphatidic acid or a salt thereof is administered every day for 5 weeks.

* * * * *